United States Patent
Myers et al.

(10) Patent No.: US 10,089,695 B1
(45) Date of Patent: Oct. 2, 2018

(54) SYSTEMS AND METHODS FOR MANAGING LONG-TERM CARE INSURANCE USING DEVICES POPULATED WITHIN A PROPERTY

(71) Applicant: STATE FARM MUTUAL AUTOMOBILE INSURANCE COMPANY, Bloomington, IL (US)

(72) Inventors: Jeremy Myers, Normal, IL (US); Brittany Boyer, Bloomington, IL (US); Dana Hunt, Normal, IL (US); David Turrentine, Bloomington, IL (US); Larry J. Ingrum, Mahomet, IL (US); Erin Olander, Bloomington, IL (US); Nicole M. Blakney, Bloomington, IL (US); Aaron C. Williams, Bloomington, IL (US)

(73) Assignee: STATE FARM MUTUAL AUTOMOBILE INSURANCE COMPANY, Bloomington, IL (US)

(*) Notice: Subject to any disclaimer, the term of this patent is extended or adjusted under 35 U.S.C. 154(b) by 150 days.

(21) Appl. No.: 14/844,594

(22) Filed: Sep. 3, 2015

Related U.S. Application Data

(60) Provisional application No. 62/077,595, filed on Nov. 10, 2014.

(51) Int. Cl.
G06Q 40/08 (2012.01)
G06Q 50/22 (2018.01)

(52) U.S. Cl.
CPC ............ G06Q 40/08 (2013.01); G06Q 50/22 (2013.01)

(58) Field of Classification Search
CPC ...................................... G06Q 40/00
USPC ............................................. 705/4
See application file for complete search history.

(56) References Cited

U.S. PATENT DOCUMENTS

| | | | | |
|---|---|---|---|---|
| 2005/0055249 | A1* | 3/2005 | Helitzer | G06Q 40/08 705/4 |
| 2007/0287416 | A1* | 12/2007 | Ku | H04M 15/00 455/406 |
| 2009/0024420 | A1* | 1/2009 | Winkler | G06Q 10/087 705/4 |

FOREIGN PATENT DOCUMENTS

WO    WO 0017800 A1 *   3/2000   ............. G06Q 40/08

\* cited by examiner

*Primary Examiner* — Cho Kwong
(74) *Attorney, Agent, or Firm* — Marshall, Gerstein & Borun LLP; Randall G. Rueth

(57) ABSTRACT

Systems and methods for managing a long-term care insurance policy associated with a property are provided. According to certain aspects, configuration data associated with a component installed within the property may be received and analyzed to determine that the component is not included in a long-term care insurance policy of the property. The component may be analyzed to determine a discount associated with the long-term care insurance policy, and the discount may then be applied to the long-term care insurance policy.

14 Claims, 10 Drawing Sheets

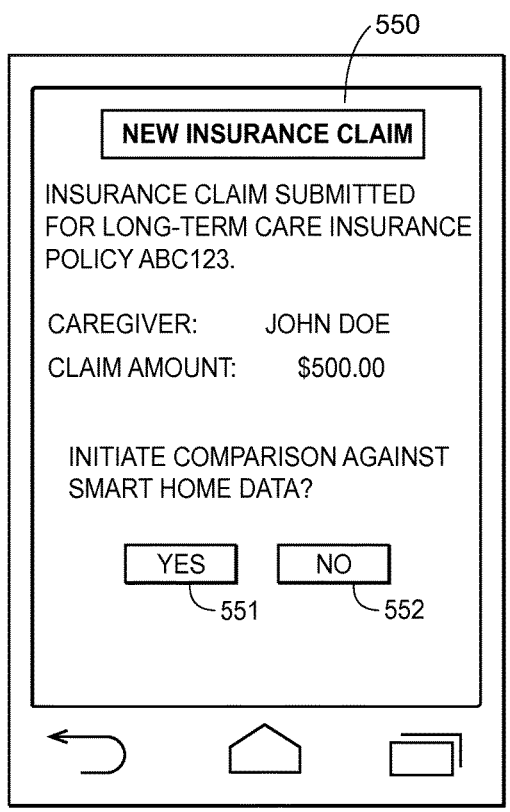
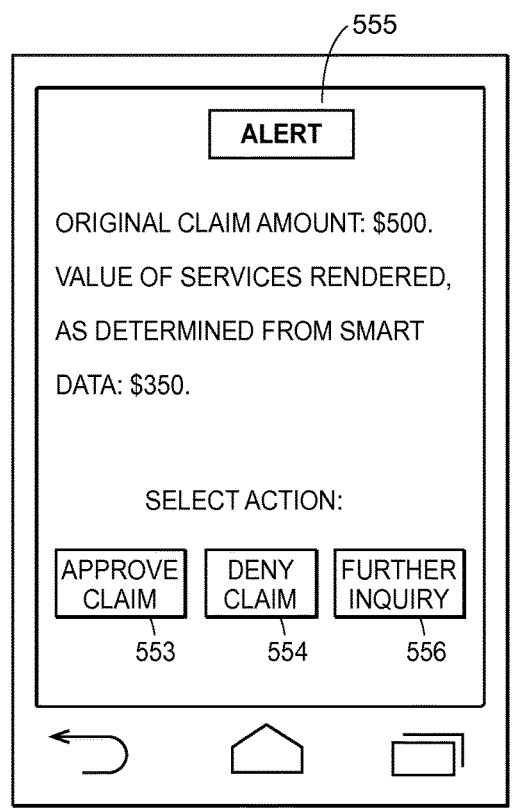
FIG. 5A  FIG. 5B

SYSTEMS AND METHODS FOR MANAGING LONG-TERM CARE INSURANCE USING DEVICES POPULATED WITHIN A PROPERTY

CROSS-REFERENCE TO RELATED APPLICATIONS

This application claims the benefit of U.S. Provisional Application No. 62/077,595, filed Nov. 10, 2014, which is incorporated by reference herein in its entirety.

FIELD OF THE DISCLOSURE

The present disclosure generally relates to managing and processing long-term care insurance policies. More particularly, the present disclosure may relate to adjusting long-term care insurance policies based on updated property configurations or modifications.

BACKGROUND

Long-term care insurance is an insurance product that helps provide for the cost of long-term care beyond a predetermined period. The insurance product covers care that is generally not covered by traditional health insurance or government-sponsored healthcare programs. Typical individuals who are covered by long-term care insurance may be unable to perform certain activities of daily living (ADLs) such as bathing and showering, dressing, eating/feeding, functional mobility, personal hygiene and grooming (e.g., brushing/combing hair), toilet hygiene, and others. There are various benefits of long-term care insurance, including the ability to cover costly out-of-pocket expenses, potential income tax deduction on premium payments, and the expertise of professional caregivers versus family and friends.

A long-term care insurance policy may cover care in a variety of environments, including home care, assisted living, adult daycare, respite care, hospice care, nursing home facilities, and Alzheimer's facilities. Generally, long-term care insurance can be more costly relative to traditional health insurance because of the complexity and difficulty of some of the services. As a result, there is a need to reduce costs both for the caregiver as well as for the policyholder. In particular, costs may generally be reduced if a policyholder's property is the primary place of care, versus a dedicated facility.

Accordingly, there is an opportunity for platforms and techniques to provide policyholders with various incentives to reduce costs associated with long-term care insurance.

SUMMARY

According to one embodiment, a computer-implemented method of managing a long-term care insurance policy associated with a property may be provided. The method may include receiving, via a communication network, configuration data associated with the property, the configuration data indicating at least one component installed within the property, examining the long-term care insurance policy to identify a listing of care-designed features installed within the property, and determining, by one or more processors, that the at least one component is not included in the listing of care-designed features. The method may further include, responsive to determining that the at least one component is not included in the listing of care-designed features, analyzing information associated with the at least one component to identify a discount associated with the long-term care insurance policy, and applying the discount to the long-term care insurance policy.

In another embodiment, a system for managing a long-term care insurance policy associated with a property may be provided. The system may include a communication module adapted to communicate data, a memory adapted to store non-transitory computer executable instructions, and a processor adapted to interface with the communication module. The processor may be configured to execute the non-transitory computer executable instructions to cause the processor to receive, via the communication module, configuration data associated with the property, the configuration data indicating at least one component installed within the property, examine the long-term care insurance policy to identify a listing of care-designed features installed within the property, and determine that the at least one component is not included in the listing of care-designed features. The processor may be further configured to, responsive to determining that the at least one component is not included in the listing of care-designed features, analyze information associated with the at least one component to identify a discount associated with the long-term care insurance policy, and apply the discount to the long-term care insurance policy.

In a further embodiment, a controller device connected to a plurality of components within a property and configured to manage a long-term care insurance policy associated with the property may be provided. The controller device may include a communication module adapted to communicate data, a memory adapted to store non-transitory computer executable instructions, and a processor adapted to interface with the communication module. The processor may be configured to execute the non-transitory computer executable instructions to cause the processor to collect, via the communication module, configuration data associated with at least one component of the plurality of components within the property, access the long-term care insurance policy to identify a listing of care-designed features installed within the property, and determine that the at least one component is not included in the listing of care-designed features. The processor may be further configured to, responsive to determining that the at least one component is not included in the listing of care-designed features, analyze information associated with the at least one component to identify a discount associated with the long-term care insurance policy, and facilitate, with an insurance provider that issued the long-term care insurance policy, the discount to the long-term care insurance policy.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIGS. 5A and 5B depict exemplary interfaces associated with detecting inaccuracies in filed insurance claims for long-term care insurance policies, in accordance with some embodiments.

DETAILED DESCRIPTION

Figure 1:
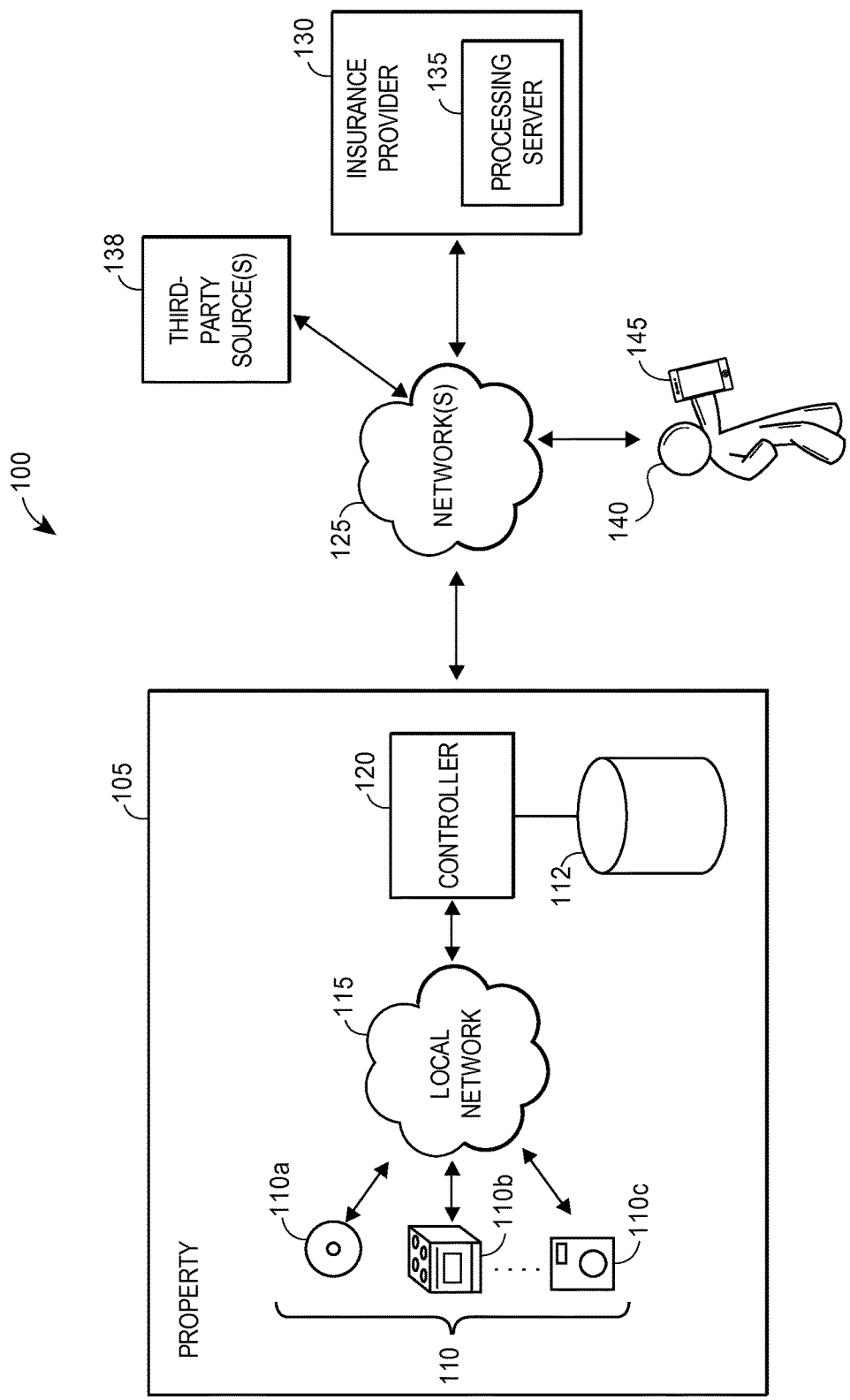
FIG. 1 depicts an exemplary environment including components and entities associated with managing and processing long-term care insurance policies associated with properties, in accordance with some embodiments.

The present embodiments may relate to, inter alia, managing long-term care insurance. Generally, a long-term care insurance policy may cover home care, assisted living, adult daycare, respite care, hospice care, nursing home facilities, and Alzheimer's facilities. A policyholder of a long-term care insurance policy is an individual who may receive various care-related services according to the coverage of the insurance policy, and a caregiver is an individual who may administer the services to the policyholder. There may be multiple caregivers who administer various services to the policyholder.

According to the present embodiments, the long-term care insurance policies may insure various care and services that may be administered within a home or property of the policyholder. For instance, the home or property may be a property owned by the policyholder, such as a primary residence or a second residence. The property may be distinguished from a professional care facility such as an assisted living facility, a nursing home, a retirement home, or the like.

Generally, a home or property may have a "smart" central controller that may be wirelessly connected, or connected via hard-wire, with various household related items, components, devices, and/or sensors. The central controller may be associated with any type of property, such as homes, office buildings, restaurants, farms, and/or other types of properties. The central controller may be in wireless or wired communication with various "smart" items or devices, such as smart appliances (e.g., clothes washer, dryer, dish washer, refrigerator, etc.); smart heating devices (e.g., furnace, space heater, etc.); smart cooling devices (e.g., air conditioning units, fans, ceiling fans, etc.); smart plumbing fixtures (e.g., toilets, showers, water heaters, piping, interior and yard sprinklers, etc.); smart cooking devices (e.g., stoves, ovens, grills, microwaves, etc.); smart wiring, lighting, and lamps; smart personal vehicles; smart thermostats; smart windows, doors, or garage doors; smart window blinds or shutters; and/or other smart devices and/or sensors capable of wireless or wired communication. Each smart device (or sensor associated therewith), as well as the central controller, may be equipped with a processor, memory unit, software applications, wireless transceivers, local power supply, various types of sensors, and/or other components. Each of the smart devices further has a location (e.g., GPS coordinates, a room of the property, an area or section of the property, or other location indication). In this regard, multiple of the smart devices may be associated with a single area or location of the property (e.g., a basement, a bathroom, a kitchen, a first floor, etc.). The central controller may connect to the various devices or products. In particular, the central controller may collect various sensor data from the devices and determine, from the sensor data, various usages or operations of the devices.

According to embodiments, certain devices or configurations of devices may reduce the complexity of some services or otherwise reduce the need to administer the services. For example, a ramp installation on a property may improve the ability of individuals to leave and enter the property. For further example, a "grab bar" installation in a bathroom may negate or reduce the need for toilet hygiene care. With conventional long-term care insurance policies, insurance providers may not be aware of certain configurations or devices within a property, and therefore may not accurately price the insurance policy. As a result, any increased costs may be passed down to the policyholders. The present embodiments describe systems and methods for automatically detecting updated configurations of devices/components, new devices/components altogether, and/or general updates to a property, and adjusting long-term care insurance policies accordingly. The systems and methods therefore may incentivize customers to include or upgrade to relevant updates or improvements in an effort to reduce insurance costs.

The systems and methods therefore offer numerous benefits. In particular, a policyholder may be incentivized to install certain devices/components or device/component configurations that will result in improved care and/or in an environment in which to easier facilitate care. Further, by implementing the systems and methods, insurance providers may automatically process insurance policy modifications, thus reducing the need for manual inspection or adjustment. It should be appreciated that further benefits to the systems and methods are envisioned.

The systems and methods discussed herein address a challenge that is particular to property management. In particular, the challenge relates to a difficulty in assessing or determining property modifications or additions and impacts thereof. This is particularly apparent when certain modifications or additions result in changes to insurance coverage. In conventional circumstances, a policyholder may not be aware that certain property modifications or additions may result in insurance modifications, or will otherwise have to manually initiate any insurance modifications as a result of property modifications or additions. In contrast, the systems and methods automatically monitor for configuration data associated with connected devices within a property and automatically process a long-term care insurances policy accordingly. Therefore, because the systems and methods employ the collection and analysis of configuration data associated with connected devices within a property, the systems and methods are necessarily rooted in computer technology in order to overcome the noted shortcomings that specifically arise in the realm of property management.

Similarly, the systems and methods provide improvements in a technical field, namely, home automation. Instead of the systems and methods merely being performed by hardware components using basic functions, the systems and methods employ complex steps that go beyond the mere concept of simply retrieving and combining data using a computer. In particular, the hardware components detect configuration data associated with connected devices within a property, assess an insurance policy associated with the property, determine how to modify the insurance policy based on the configuration data, and modify the insurance policy accordingly. This combination of elements further impose meaningful limits in that the operations are applied to improve home automation by detecting existing and updated configuration data, and facilitating appropriate insurance processing in a meaningful and effective way.

FIG. 1 depicts an example environment 100 including components and entities associated with a property and processing insurance policies associated therewith. Although FIG. 1 depicts certain entities, components, and devices, it should be appreciated that additional or alternate entities and components are envisioned.

As illustrated in FIG. 1, the environment 100 includes a property 105 that contains a controller 120 and a plurality of devices 110 that may be each connected to a local communication network 115. Each of the plurality of devices 110 may be a "smart" device that is configured with one or more sensors capable of sensing and communicating operating data associated with the corresponding device 110. As shown in FIG. 1, the plurality of devices 110 may include a smart alarm system 110a, a smart stove 110b, and a smart washing machine 110c. Each of the plurality of devices 110 may be located within or proximate to the property 105 (generally, "on premises"). Although FIG. 1 depicts only one property 105, it should be appreciated that multiple properties are envisioned, each with its own controller and devices. Further, it should be appreciated that additional or fewer devices may be present in the property 105. In some cases, the plurality of devices 110 may be purchased from a manufacturer with the "smart" functionally incorporated therein. In other cases, the plurality of devices 110 may have been purchased as "dumb" devices and subsequently modified to add the "smart" functionality to the device. For example, a homeowner may purchase an alarm system that installs sensors on or near a door to detect when a door has been opened and/or unlocked. Throughout this specification, the terms "device" and "component" may be used interchangeably. In some implementations, a device (such as one of the devices 110) may be composed of a set of components. For example, a stove may have several components such as, for example, burners, a door, metal racks, a bottom drawer, and/or the like.

The plurality of devices 110 may be configured to communicate with a controller 120 via the local communication network 115. The local communication network 115 may facilitate any type of data communication between devices and controllers located on or proximate to the property 105 via any standard or technology (e.g., LAN, WLAN, any IEEE 802 standard including Ethernet, and/or others). The local communication network 115 may further support various short-range communication protocols such as Bluetooth®, Bluetooth® Low Energy, near field communication (NFC), radio-frequency identification (RFID), and/or other types of short-range protocols.

According to aspects, the plurality of devices 110 may transmit, to the controller 120 via the local communication network 115, operational data gathered from sensors associated with the plurality of devices 110. The operational data may be audio data, image or video data, status data, and/or other data or information. For example, the operational data may indicate that a window has been shattered; the presence of a person, fire, or water in a room; the sound made near a smart device; and/or other information pertinent to an operation state or status of the plurality of devices 110. For further example, the operational data may include motion data that may indicate whether any individuals are within the property 105 (i.e., whether the property 105 is occupied or unoccupied). The operational data may include a timestamp representing the time that the operational data was recorded.

In some cases, the plurality of devices 110 may transmit, to the controller 120, various other data and information associated with the plurality of devices 110. In particular, one of the plurality of devices 110 may, when installed or otherwise located within the property, automatically connect to the controller 120 and may transmit various identification and configuration data. For example, the configuration data may include various information associated with the corresponding device 110, such as model information, settings, dimensions, age, location, and/or other information. It should be appreciated that an individual may manually interface with the controller 120 to input various configuration information associated with the plurality of devices 110. It should further be appreciated that the controller 120 may periodically request the plurality of devices 110 for respective configuration information.

The controller 120 may be coupled to a database 112 that stores various operational data and information associated with the plurality of devices 110. In particular, the database 112 may store any operation data that is collected from the plurality of devices 110, as well as any configuration data (e.g., settings, dimensions, model information, etc.) associated with the plurality of devices 110. Although FIG. 1 depicts the database 112 as coupled to the controller 120, it is envisioned that the database 112 can be maintained in the "cloud" such that any element of the environment 100 capable of communicating over either the local network 115 or one or more other networks 125 may directly interact with the database 112. In some embodiments, the database 112 organizes the operational data according to which individual device 110 the data is associated and/or the room or subsection of the property in which the data was recorded. Further, the database 112 may maintain an inventory list that includes the plurality of devices 110 as well as various data and information associated with the plurality of devices 110 (e.g., locations, replacement costs, etc.).

The controller 120 may be configured to communicate with other components and entities such as an insurance provider 130 and various third party source(s) 138 via the network(s) 125. According to embodiments, the network(s) 125 may facilitate any data communication between the controller 120 located on the property 105 and entities or individuals remote to the property 105 via any standard or technology (e.g., GSM, CDMA, TDMA, WCDMA, LTE, EDGE, OFDM, GPRS, EV-DO, UWB, IEEE 802 including Ethernet, WiMAX, and/or others). In some cases, both the local network 115 and the network 125(s) may utilize the same technology.

Generally, the insurance provider 130 may be any individual, group of individuals, company, corporation, or other type of entity that may issue insurance policies for customers. In particular, the insurance provider 130 may issue a long-term care insurance policy for one or more individuals associated with the property 105. The insured individual may reside in the property 105, and may be the owner of the property 105 or otherwise associated with the property 105. The insurance provider 130 may include one or more processing server(s) 135 configured to facilitate the functionalities as discussed herein. Although FIG. 1 depicts the processing server 135 as a part of the insurance provider 130, it should be appreciated that the processing server 135 may be separate from (and connected to or accessible by) the insurance provider 130. Further, although the present disclosure describes the systems and methods as being facilitated in part by the insurance provider 130, it should be appreciated that other non-insurance related entities may implement the systems and methods. The third-party source(s) 138 may be any entity or component capable of communicating with the insurance provider 130. For example, one of the third-party sources 138 may be a manufacturer or supplier of various of the devices 110 in the property 105. It should be appreciated that additional third-party source(s) 138 are envisioned.

The controller 120 may also be in communication, via the network(s) 125, with an electronic device 145 associated with an individual 140. In embodiments, the individual 140 may have an insurance policy (e.g., a long-term care insurance policy) for the property 105 or a portion of the property 105, or may otherwise be associated with the property 105 (e.g., the individual 140 may live in the property 105). In other embodiments, the individual 140 may be a caregiver who administers services according to long-term care insurance policies. The electronic device 145 may be a smartphone, a desktop computer, a laptop, a tablet, a phablet, a smart watch, smart glasses, or any other electronic device. In some implementations, the insurance provider 130 may communicate, to the individual 140 via the electronic device 145, information associated with a long-term care insurance policy, as well as receive selections and modifications associated with the policy.

According to aspects, the controller 120 may detect the presence of the devices 110 and may retrieve configuration data associated with the devices 110. The configuration data may indicate any update(s) to the devices 110 as well the identifications of any new devices 110. For example, the controller 120 may determine that a light switch has been installed at a height accessible by an individual in a wheelchair. The controller 120 may communicate the configuration data to the insurance provider 130, and the insurance provider 130 may determine, based on the configuration data, that there is an associated discount or benefit available for the long-term care insurance policy. The insurance provider 130 may apply the discount or benefit to the long-term care insurance policy. For example, the installation of the light switch may result in a discount of $5 to the monthly premium for the long-term care insurance policy.

In other aspects, the insurance provider 130 may receive an insurance claim submission from a caregiver. The insurance claim may indicate a set of services that are purportedly administered, by a caregiver, to the policyholder within the property 105. Responsive to receiving the claim submission, the insurance provider 130 may request the controller 120 to retrieve operation/operational data from the plurality of devices 110, where the requested operation data may correspond to the set of services indicated in the insurance claim. The controller 120 may receive the operation data from the plurality of devices 110 and send the operation data to the insurance provider 130, and the insurance provider 130 may analyze the operation data to determine a set of services that were actually performed within the property 105. The insurance provider 135 may therefore identify any discrepancies between the set of purported services and the set of actual services, and process or deny the insurance claim accordingly.

Generally, any long-term care insurance policies that cover services that may be administered to a policyholder within the property 105 may be priced differently from other long-term care insurance policies associated with dedicated facilities such as nursing homes, assisted living facilities, and/or the like. Further, the embodiments envision a service or tool that may identify various services and/or products that are associated with long-term care insurance. In particular, the service or tool may provide information associated with various products, including services covered by the product, pricing, duration, and/or the like. The service or tool may further connect individuals seeking insurance to providers as well as make recommendations for particular insurance products. An individual may interface with the service or tool to input relevant information such as, for example, recent lab values from physical checkups, notes from charts, medical history information, current information about the property 105, current health of the individual, any health concerns, nutrition and diet information, and/or other relevant information.

As described herein, the policyholder of a long-term care insurance policy may be an individual who receives long-term care services from a caregiver. It should be appreciated that the policyholder may also be an individual associated with the individual (or patient) that receives the long-term care services. For example, an individual may purchase a long-term care insurance policy on behalf of a parent. In this scenario, the insurance provider may enable the policyholder to access various data associated with the individual receiving care. For example, the policyholder may access data associated with the controller 120 and/or the plurality of devices 110. Further, the policyholder may access various telematics data associated with a vehicle of the individual receiving care. It should be appreciated that other data access channels are envisioned.

Figure 2:
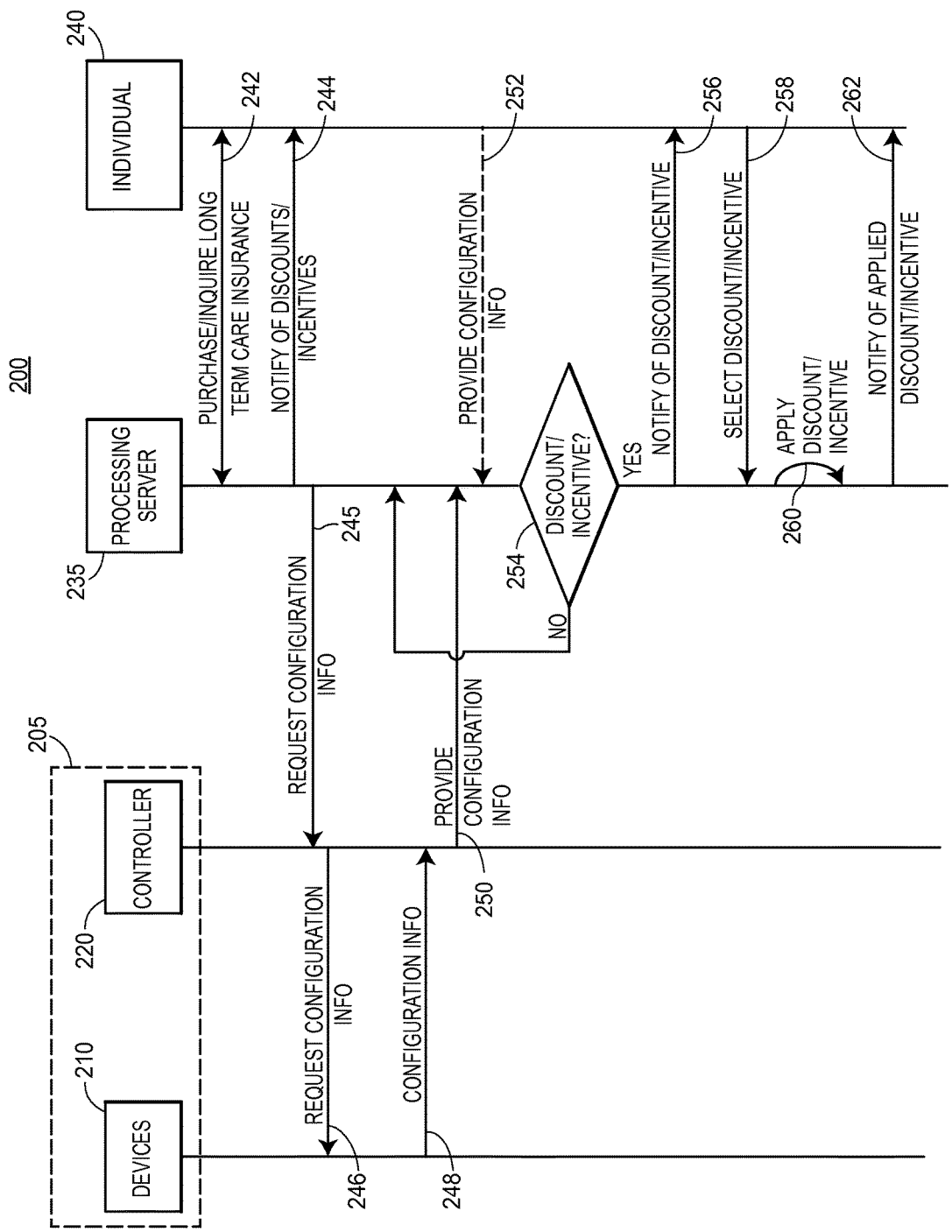
FIG. 2 depicts an exemplary signal diagram associated with identifying and processing discounts for long-term care insurance policies, in accordance with some embodiments.

Referring to FIG. 2, illustrated is an exemplary signal diagram 200 associated with managing long-term care insurance policies associated with a property 205. The property 205 is populated with a set of devices 210. In particular, FIG. 2 includes the set of devices 210 (such as the plurality of devices 110 as described with respect to FIG. 1), a controller 220 (such as the controller 120 as described with respect to FIG. 1), a processing server 235 (such as the processing server 135 as described with respect to FIG. 1) that may be associated with an insurance provider, and an individual 240 (such as the individual 140 as described with respect to FIG. 1). The individual 240 may have an associated electronic device capable of communication with the other components, such as the electronic device 145 as described with respect to FIG. 1.

The individual 240 may be associated with the property 205 in some capacity. In particular, the individual 240 may reside or live in the property 205 and/or may be the policyholder for (or have access to) a long-term care insurance policy issued by the insurance provider and associated with the property 205. It should be appreciated that the smart devices 210 are populated within the property 205 or in proximity to the property 205.

The signal diagram 200 may begin when the individual 240 inquires about and/or purchases (242) a long-term care insurance policy. The terms of the long-term care policy may be at least in part based on the devices 210 and/or on other characteristics of the property 205. Generally, the more that the property 205 (and/or the devices 210 thereof) is tailored to the care of an individual (such as the individual 240) who occupies the property or otherwise benefits from the long-term care policy, the less the premium associated with the long-term care policy. Of course, the terms of the long-term care policy may also be based on other factors associated with the individual, such as age, gender, health, and/or the like, as known in the art. In some scenarios, when applying for the long-term care insurance policy, the individual 240 may detail various devices, objects, configurations, layouts, and/or the like that are associated with the property 205 and the devices 210, and that may be a factor to the coverage, terms, and/or premium of the long-term care insurance policy.

As part of the purchase of the long-term care insurance policy, the processing server 235 may identify or determine various modifications to the property 205 that may result in discounts or incentives for the individual 240. For example, the property 205 may not currently have any "grab bars" installed in its bathrooms, and the processing server 235 may determine that adding grab bars to each of the bathrooms will result in a $10 discount to the premium rate of the long-term care insurance policy. Generally, the various modifications are based on the current devices, objects, configurations, and/or layouts of the property 105, such that the various modifications are able to indeed improve and/or alter the current devices, objects, configurations, and/or layouts of the property 105. It should be appreciated that the processing server 235 may identify the modifications according to various algorithms, calculations, and/or techniques. Further, it should be appreciated that the processing server 235 may identify the discounts or incentives associated with the modifications according to various algorithms, calculations, and/or techniques. In some aspects, the discounts or incentives may have time periods or expiration dates associated with them. The processing server 235 may notify (244) the individual 240 of the discounts or incentives, along with a description of the modifications that may be completed to qualify for the discounts or incentives.

According to embodiments, the individual 240 (or someone else) may perform or otherwise facilitate the modifications originally identified by the processing server 235, or in some cases any modifications that are not originally identified by the processing server 235. The modifications may be performed or facilitated after the long-term care insurance has been purchased, whereby the modifications may qualify the individual 240 for the discounts or incentives identified by the processing server 235, or in some cases any discounts or incentives that may be dynamically identified or calculated. In implementations, the processing server 235 may request (245) the controller 220 to provide configuration information associated with the devices 210. As a result, the controller 220 may request (246) configuration information from the devices 210.

Generally, the configuration information may indicate settings, parameters, configurations, dimensions, versions, and/or other information associated with the devices 210. At least some of the configuration information may be related to a modification or update to an existing device, or may be related to a new device within the property 205. The controller 220 may periodically request for configuration information from the devices 210 or may request the configuration information in response to a trigger (e.g., a user request or a request from the processing server 235). The appropriate device(s) 210 may provide (248) the configuration information to the controller 220, wherein the configuration information may include any settings, characteristics, parameters, and/or the like that are associated with the appropriate devices(s) 210. In some embodiments, the appropriate device(s) 210 may automatically provide the configuration information, or a user may cause the appropriate device(s) 210 to provide the configuration information. After receiving the configuration information, the controller 220 may provide (250) the configuration information to the processing server 235.

In some other scenarios, the individual 240 may provide (252) configuration information related to the devices 210 to the processing server 235. The individual 240 can, in some situations, fill out and submit a form that details the configuration information. In other situations, the electronic device of the individual 240 may automatically collect the configuration information from the devices 210 themselves (e.g., via a short-range communication). The individual 240 (or more particularly, the electronic device of the individual 240) may also provide additional data that supplements the configuration information. For example, if a stairway of the property 205 has been reconfigured to better accommodate elderly individuals, the individual 240 may supplement an indication of the reconfigured stairway with an image of the reconfigured stairway.

After receiving any configuration information from the controller 220 and/or the individual 240, the processing server 235 may analyze the configuration information to determine (254) whether there is an applicable discount or incentive. In embodiments, the processing server 235 may determine that the device 210 complies with a specified modification or configuration, and therefore qualifies for the applicable discount or incentive. For example, the processing server 235 may determine, from received configuration information, that a front doorway to the property 205 has been widened to 48 inches, thus improving the ability for the doorway to accommodate wheelchairs. The widening of the door to a specified threshold (e.g., 46 inches) may qualify for a 5% premium discount. Accordingly, the processing server 235 may determine that the front doorway meets the specified threshold and that a 5% premium discount should be applied to a long-term care insurance policy of the individual 240. In some cases, if a discount or incentive is not detected ("NO") processing may return to gathering and providing configuration information.

If a discount or incentive is detected ("YES"), the processing server 235 may notify (256) the individual 240 of the discount or incentive. In particular, the processing server 235 may provide a notification to the individual 240 via the electronic device of the individual 240 (such as via a dedicated application). It should be appreciated that other notification channels are envisioned (e.g., e-mail, telephone call, SMS message, etc.). After receiving the notification of the discount or incentive, the individual 240 may be able to select to apply the discount or incentive. In some instances, the individual 240 may not want an offered discount or incentive (such as in cases in which the individual 240 is accumulating points or rewards in the hope of qualifying for a more substantial discount or incentive). Of course, if the individual 240 wants the offered discount or incentive, the individual 240 may select (258) the discount or incentive.

In response to the user selecting the discount or incentive, the processing server 235 may apply (260) the discount/incentive to the long-term care insurance policy of the individual 240. Further, the processing server 235 may notify (262) the individual 240 of the applied discount or incentive. The processing server 235 may notify the individual 240 of the applied discount or incentive via the same or different channel as the notification of (256).

Figure 3:
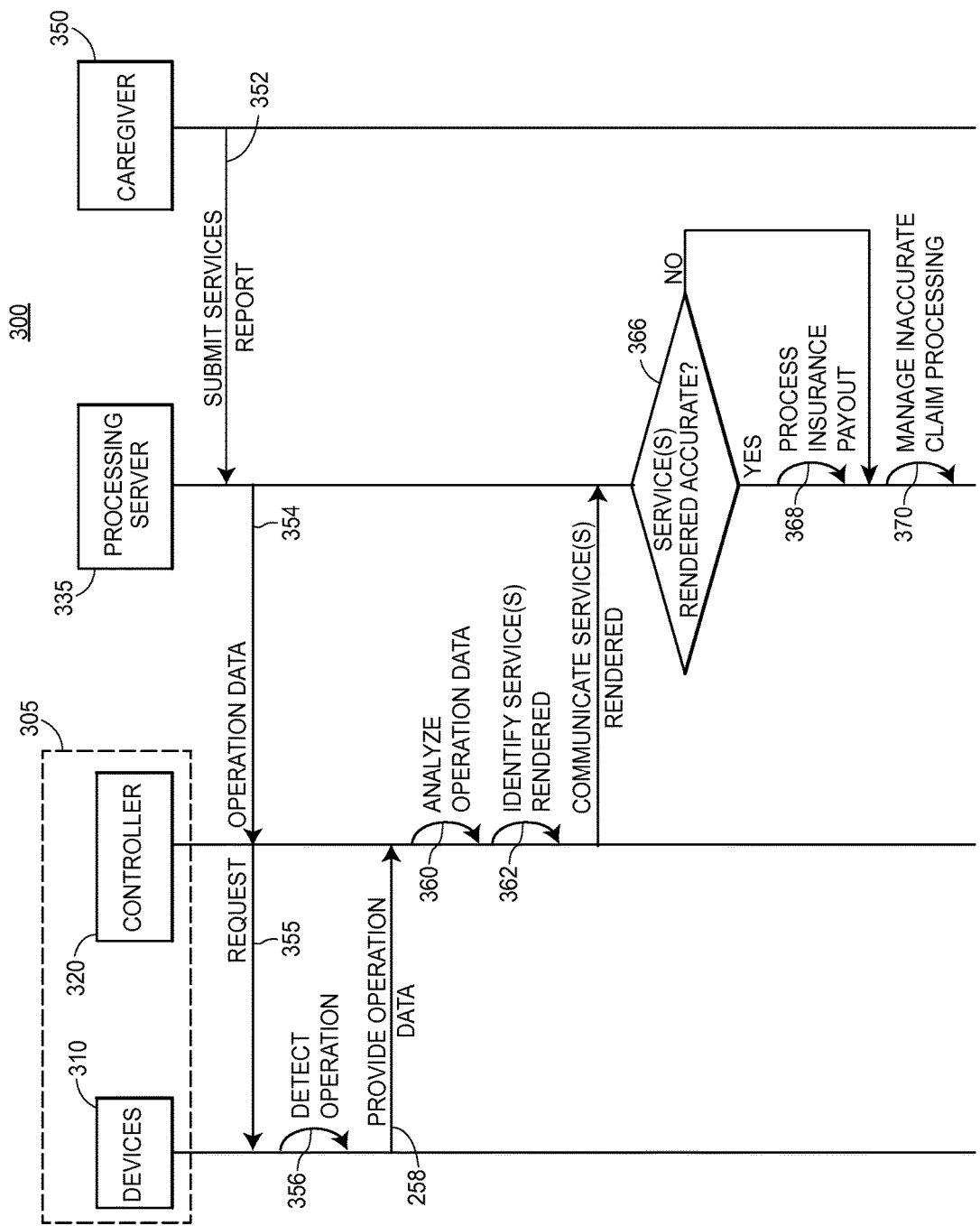
FIG. 3 depicts an exemplary signal diagram associated with detecting inaccuracies in filed insurance claims for long-term care insurance policies, in accordance with some embodiments.

Referring to FIG. 3, illustrated is an exemplary signal diagram 300 associated with detecting claim inaccuracies in long-term care insurance policies associated with a property 305 that may be populated with a set of devices 310. In particular, FIG. 3 includes the set of devices 310 (such as the plurality of devices 110 as described with respect to FIG. 1), a controller 320 (such as the controller 120 as described with respect to FIG. 1), a processing server 335 (such as the processing server 135 as described with respect to FIG. 1) that may be associated with an insurance provider, and a caregiver 350. The caregiver 350 may have an associated electronic device capable of communication with the other components, such as the electronic device 145 as described with respect to FIG. 1.

The caregiver 350 may be associated with the property 305 in some capacity. In particular, the caregiver 350 may be a caregiver for an individual who resides or lives in the property 305. The individual who resides or lives in the property 305 may be the policyholder for (or have access to) a long-term care insurance policy issued by the insurance provider and associated with the property 305. Further, the caregiver 350 may submit insurance claims related to the care of the individual which the processing server 335 may approve or reject. If the processing server 335 approves a claim, a monetary amount specified in the claim is paid out from the insurance provider to the caregiver 350. Of course, the insurance provider has an interest in reducing fraudulent claims on the part of the caregiver 350. In particular, the caregiver 350 may falsely claim that he or she administered a specific service to an individual, and may attempt to collect monies owned for that specific service. According to embodiments, the service may involve use of one or more of the devices 310. For example, one of the devices 310 may be a valve sensor for a shower that is configured to monitor when the shower is turned on and off. It should be appreciated that the devices 310 are populated within the property 305 or in proximity to the property 305.

The signal diagram 300 may begin when the caregiver 350 submits (352) an insurance claim including a services report to the processing server 335. By submitting the services report, the caregiver 350 is claiming that he/she performed or administered the services indicated in the services report, and is expecting the insurance provider to distribute a corresponding monetary amount to the caregiver 350. According to embodiments, the services report may include a listing of services that the caregiver 350 claims to have administered to the patient/individual having the long-term care insurance policy, whereby the services are covered by the long-term care insurance policy. The services report may also include a monetary amount associated with each of the administered services. For example, the caregiver 350 may indicate that he/she bathed a patient (a service having an associated monetary amount of $50), cooked dinner for the patient (a service having an associated monetary amount of $40), and cleaned the property 205 (a service having an associated monetary amount of $100), for a total amount of $190.

In some implementations, the processing server 335 may determine, by examining the services report, which of the services are detectable or verifiable by data from the devices 310. For example, the processing server 335 may determine that a bathing service is verifiable by one or more bathroom devices, and that a clothes change service is not verifiable by the devices 310 of the property 305. In determining which of the services are detectable or verifiable by data from the devices 310, the processing server 235 may identify the devices 310 of the property from a data record associated with the long-term care insurance policy.

The processing server 335 may request (354) the controller 320 to provide operation data and/or an indication of actual services performed by the caregiver 350 in the property 305. In some embodiments, the processing server 335 may submit the request in response to receiving the services report from the caregiver 350. In other embodiments, the processing server 335 may periodically (e.g., daily, weekly, etc.) request the controller 320 to provide operation data and/or the indication of actual services performed. Because the devices 310 are actually generating the operation data, the controller 320 may relay (355) the request to the devices 310. In aspects, the request may specify specific operation data from specific devices 310, which may be based on the services specified in the services report. For example, if the services report specifies that the caregiver 350 bathed the individual, then the processing server 335 may request operation data related to any devices 310 associated with a bathtub. In other aspects, the request may specify operation data from a certain time period. For example, if the services report specifies that the caregiver 350 performed a specific service at a specific time, then the processing server 335 may request appropriate operation data corresponding to the specific time (e.g., operation data that is within a range of the specific time).

After receiving the request from the controller 320, the devices 310 may collect or otherwise detect (356) the operation data. The operation data may correspond to at least a portion of the devices 310 associated with the services specified in the services report. Further, the operation data may have a specific time (or time range) corresponding to a specific time specified in the services report. After detecting or collecting the operation data, the devices 310 may provide (358) the operation data to the controller 320. In embodiments, the devices 310 may communicate with the controller 320 via a local network of the property 305.

After receiving the operation data, the controller 320 may analyze (360) the operation data. In particular, the controller 320 may identify activations/deactivations of certain of the devices 110, calculate time periods during which certain of the devices 110 are activated, identify presence information from motion detection data, and/or other determinations. The controller 320 may also identify (362), based on the operation data analysis, any service(s) actually rendered or administered. In particular, the controller 320 may determine that a certain service was administered if one or more corresponding devices 310 associated with the certain service was activated for a requisite period of time. For example, the controller 320 may determine that a meal was prepared based on all of a stovetop, an oven, and a microwave being activated within a certain time. In embodiments, the controller 320 may make any determinations with or without incorporating any time factors. After identifying any service(s) rendered, the controller 320 is configured to communicate (364) identifications of the services rendered to the processing server 335. Although FIG. 3 depicts the controller 210 analyzing the activity data and identifying the service(s) rendered, it should be appreciated that the processing server 335 is also configured to perform one or more of the analyzing and identifying. In particular, the controller 320 may provide, to the processing server 335, the operation data received from the devices 310, and the processing server 335 may determine the actual services rendered from the operation data.

The processing server 335 may determine (366) whether the services indicated in the services report are accurate. In particular, the processing server 335 may compare the services indicated in the service report to the rendered services identified from the operation data. In some implementations, if each of the services indicated in the services report is included in the identified rendered services, then the processing server 335 may deem the services report to be accurate. In other implementations, the processing server 335 may determine that the services report is accurate if a threshold amount of the identified rendered services is indicated in the services report. Of course, some of the services that are indicated in the services report may not be able to be identified from the activity data. For example, the devices 310 may not be capable of determining whether the caregiver 350 changes the patient's clothes. Accordingly, the processing server 335 may perform the determination of (366) for those services that are detectable or verifiable by the operation data of the devices 310.

The processing server 335 may also be configured to determine whether the claimed monetary amount of damage in the services report is accurate. In particular, the processing server 335 can identify, from terms of the long-term care insurance policy, a default rate for each of the various services identified in the services report, and compare the default rate(s) to the claimed amount(s) of the service(s) indicated in the services report. If the claimed monetary amount of damage is inaccurate (e.g., different from the calculated default amount by a threshold amount), then the processing server 335 may flag or deny the claim.

If the processing server 335 determines that the services indicated in the services report are accurate in (366) ("YES"), the processing server 335 may process (366) the claim and the corresponding insurance payout, as understood in the art. Processing of the signal diagram 300 may then end or proceed to any other functionality. In contrast, if the processing server 335 determines that the services indicated in the services report are not accurate ("NO"), the processing server 335 may manage (370) processing of the inaccurate insurance claim accordingly. In some situations, the processing server 335 may deny the insurance claim. In other situations, the processing server 335 may flag the insurance claim for further information. In particular, the processing server 335 may request more information from the caregiver 350, whereby the caregiver 350 may provide additional or alternate information. The processing server 335 may eventually process or deny any modified insurance claim.

Figure 4A:
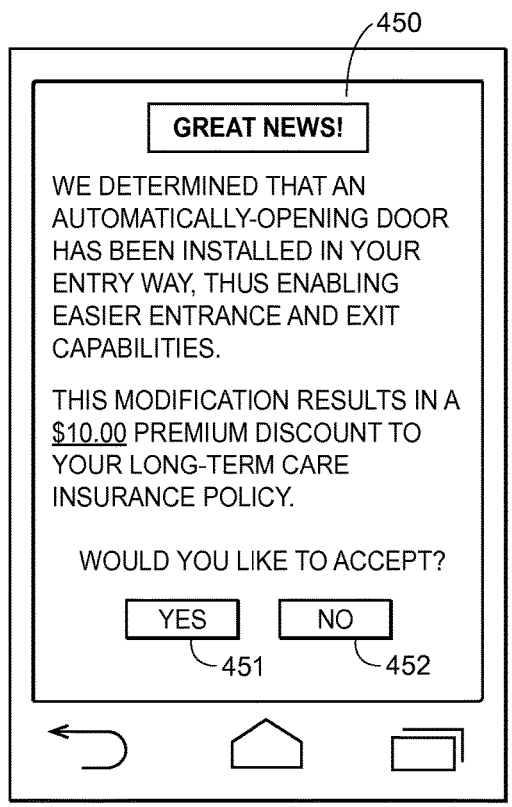
FIGS. 4A-4C depict exemplary interfaces associated with identifying and processing discounts for long-term care insurance policies, in accordance with some embodiments.
Figure 4B:
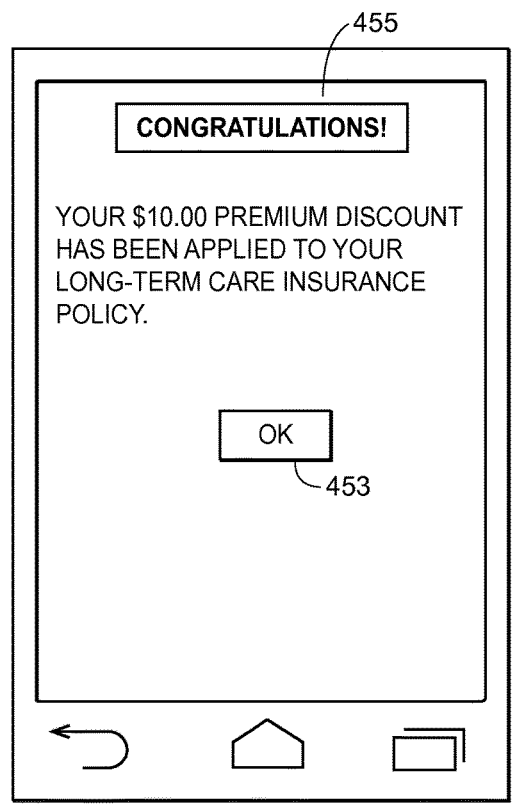
Figure 4C:
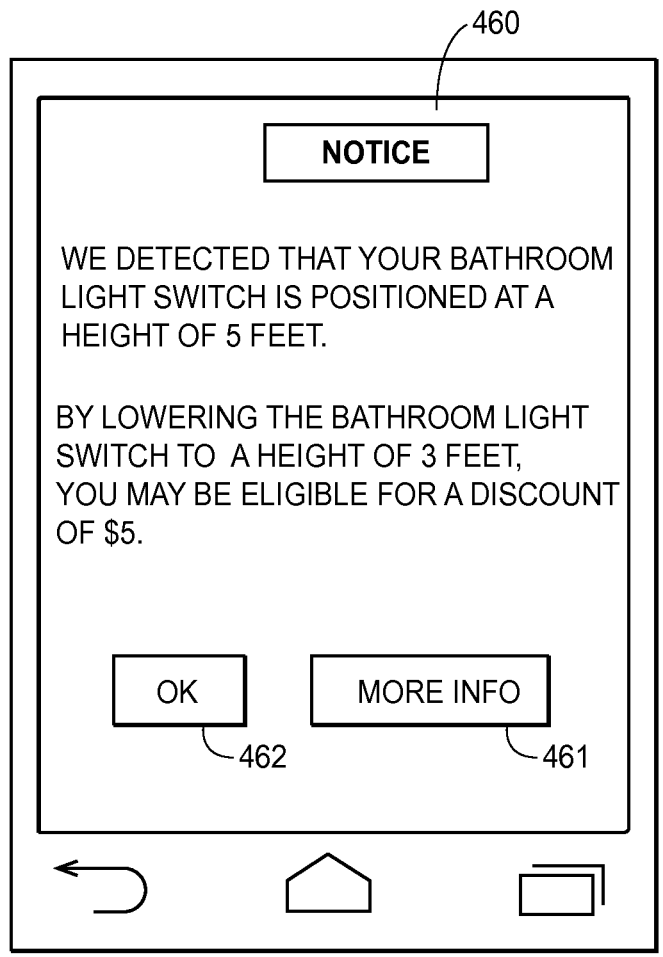

FIGS. 4A-4C illustrate exemplary interfaces associated with detecting property modifications and policy modifications associated therewith. An electronic device (e.g., a smartphone) may be configured to display the interfaces and receive selections and inputs via the interfaces. For example, a dedicated application associated with an insurance provider (or with a controller) and that is configured to operate on the electronic device may display the interfaces. Further, the interfaces may be accessed by a customer having a long-term care insurance policy. It should be appreciated that the interfaces are merely examples and that alternative or additional content is envisioned.

FIG. 4A illustrates an interface 450 including details related to detecting a modification to a property. In particular, the modification is an installation of an automatically-opening door in the entryway to the property. The insurance provider may determine the modification via the receipt of sensor or configuration data from the property, as discussed herein. The insurance provider may further determine that the installation of the automatically-opening door results in a $10.00 discount to the premium of the long-term insurance policy.

The interface 450 enables the customer to select whether to accept the premium discount via a "YES" selection 451 and a "NO" selection 452. If the customer selects the "NO" selection 452, the terms and premium of the insurance policy may remain unchanged. If the customer selects the "YES" selection 451, the insurance policy may process the corresponding premium discount. After the premium discount is processed, the electronic device may display an interface 455 as depicted in FIG. 4B. The interface 445 informs the customer that the $10.00 premium discount has been applied to the insurance policy. The customer may select to dismiss the interface 445 via an "OK" selection 353.

FIG. 4C illustrates an interface 460 including details related to a potential property modification associated with a property. In particular, a hardware controller may gather sensor or device data indicating that a particular configuration. As illustrated in the interface 460, the detected configuration is a bathroom light switch positioned at a height of five (5) feet. In addition to detecting modifications that may result in insurance saving, the systems and methods may detect existing configurations and identify modifications to those configurations that may result in benefits to customers or policyholders, such as discounts, premium reductions, and other incentives.

The interface 460 further informs the customer that by lowering the bathroom light switch to a height of three (3) feet, that the customer may be eligible for a $5 discount on the associated long-term care insurance policy. The interface 460 includes a "MORE INFO" selection 461 that enables the customer to view more information related to the potential modification and potential insurance policy incentives. The interface 460 further includes an "OK" selection 462 that enables the customer to dismiss the interface 460.

FIGS. 5A and 5B illustrate exemplary interfaces associated with processing an insurance claim related to a long-term care insurance policy. An electronic device (e.g., a smartphone) may be configured to display the interfaces and receive selections and inputs via the interfaces. For example, a dedicated application associated with an insurance provider (or with a controller) and that is configured to operate on the electronic device may display the interfaces. Further, the interfaces may be accessed by an employee or another individual associated with an insurance provider, such as a claims processor. It should be appreciated that the interfaces are merely examples and that alternative or additional content is envisioned.

FIG. 5A illustrates an interface 550 that details a filed insurance claim related to a long-term care insurance policy (as shown: example policy ABC123). The filed insurance claim indicates that a caregiver John Doe has submitted a claim in the amount of $500. It should be appreciated that the interface 550 may also detail which of the service(s) that the caregiver performed that equate to the claimed amount of $500. The interface 550 enables the individual to select to initiate a comparison against smart home data via a "YES" selection 551 and a "NO" selection 552. If the individual selects the "NO" selection 552, the electronic device may dismiss the interface 550 and proceed to other functionality.

If the individual selects the "YES" selection 551, the electronic device may initiate a retrieval of data from the set of devices populated within the property, as discussed herein. Further, based on any retrieved data, the electronic device may identify a set of services that were actually performed in the property, as well as a value of the set of those services. The electronic device may then display an exemplary interface 555 as depicted in FIG. 5B. As illustrated in FIG. 5B, the interface 555 indicates that the original claim amount totals $500 and that the value of the set of actual services totals $350, resulting in a discrepancy of $150. Accordingly, the caregiver may not be entitled to the entire $500 claimed amount.

The interface 555 includes various selections that enable the individual to take various actions associated with the insurance claim: an approve claim selection 553, a deny claim selection 554, and a further inquiry selection 556. If the individual selects the approve claim selection 553, the insurance provider can approve the insurance claim. If the individual selects the deny claim selection 554, the insurance provider can deny the insurance claim. If the individual selects the further inquiry selection 556, the electronic device may facilitate a communication with the customer, in an attempt to clarify certain information, obtain additional information, or otherwise attempt to account for the calculated discrepancy.

Figure 6:
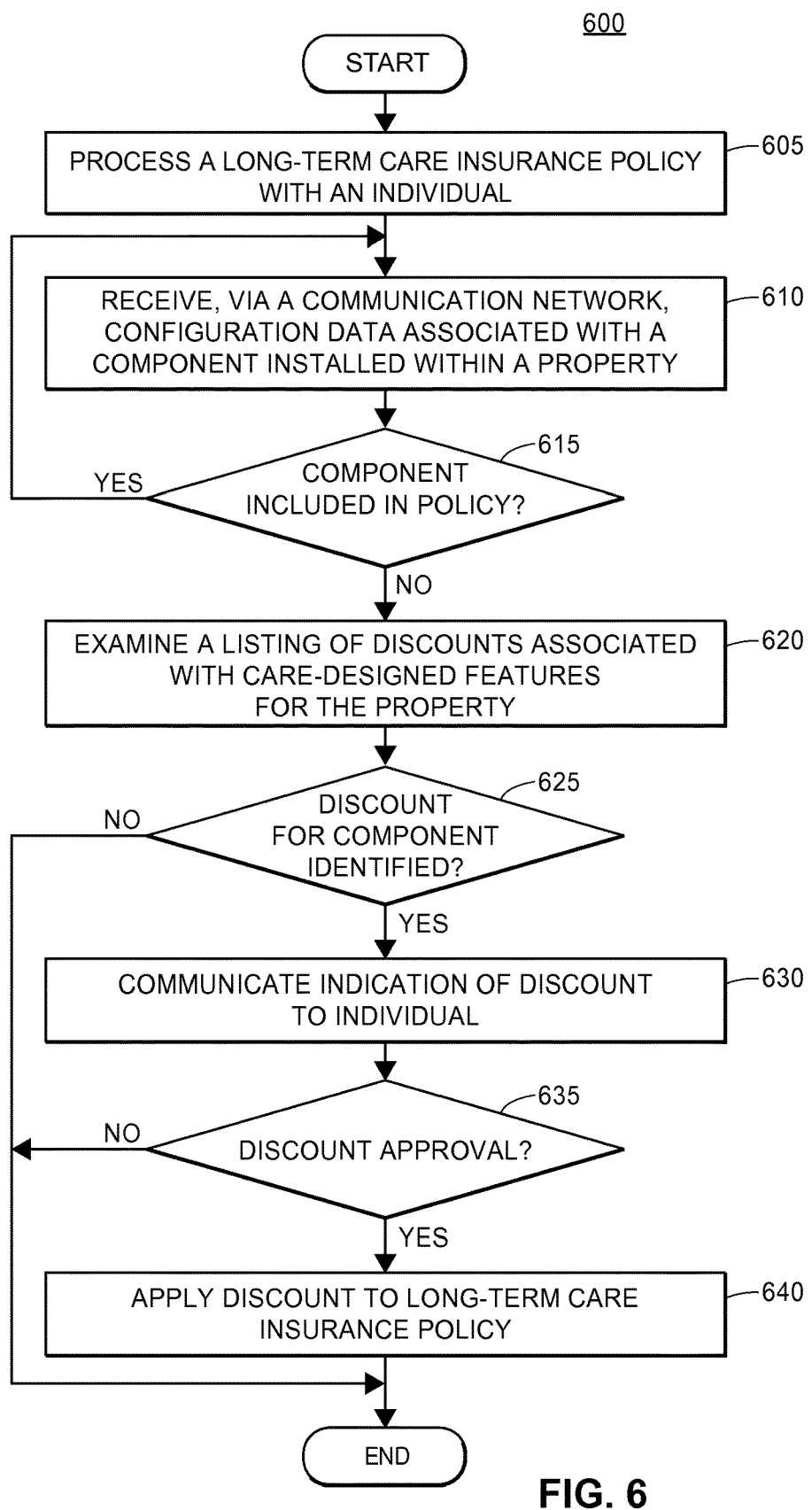
FIG. 6 depicts an exemplary flow diagram associated with identifying and processing discounts for long-term care insurance policies, in accordance with some embodiments.

Referring to FIG. 6, depicted is a block diagram of an exemplary method 600 of managing a long-term care insurance policy held by an individual residing in a property. According to embodiments, the property may be populated with a plurality of devices and a controller (such as the controller 120 as discussed with respect to FIG. 1) connected to the plurality of devices. The method 600 may be facilitated by an insurance provider (such as the insurance provider 130 as discussed with respect to FIG. 1) in communication with the controller 120 as well as the individual.

The method 600 may begin when the insurance provider processes (block 605) a long-term care insurance policy with the individual. In particular, the long-term care insurance policy may cover various services that a caregiver may administer to the individual within the property. Further, the long-term care insurance policy may be priced according to various devices or components that, at the time the policy is processed, are implemented or otherwise located within or proximate to the property.

The insurance provider may receive (block 610), via a communication network, configuration data associated with a component installed within a property. In embodiments, the insurance provider may receive the configuration data from the individual, or from the controller of the property. The configuration data may indicate an update to one of the existing components or devices within the property, and/or may indicate a new component or device within the property. The insurance provider may determine (block 615) whether the component is included in the long-term care insurance policy. In particular, the insurance provider may determine whether the insurance policy accounts for the component or device indicated in the configuration data. If the component is already included in the insurance policy ("YES"), processing may return to block 610 or proceed to other functionality.

If the component is not included in the insurance policy ("NO"), the insurance provider may examine (block 620) a listing of discounts associated with care-designed features for the property and determine (block 625) whether there is a discount for the component. In particular, the care-designed features may improve the ability for caregivers (or others) to administer services to the individual, or improve the ability for the individuals to take care of themselves. Further, each of the care-designed features may have an associated discount. For example, installing automatic open/close front doors may result in a $10 policy premium discount. If there is not a discount for the component ("NO"), processing may end or proceed to other functionality.

If there is a discount for the component ("YES"), the insurance provider may communicate (block 630) an indication of the discount to the individual. After receiving the indication, the individual may accept or reject the discount. Accordingly, the insurance provider may determine (block 635) whether the individual has approved the discount. If the individual has not accepted the discount ("NO"), processing may end or proceed to other functionality. If the individual has accepted the discount ("YES"), the insurance provider may apply (block 640) the discount to the long-term care insurance policy.

Figure 7:
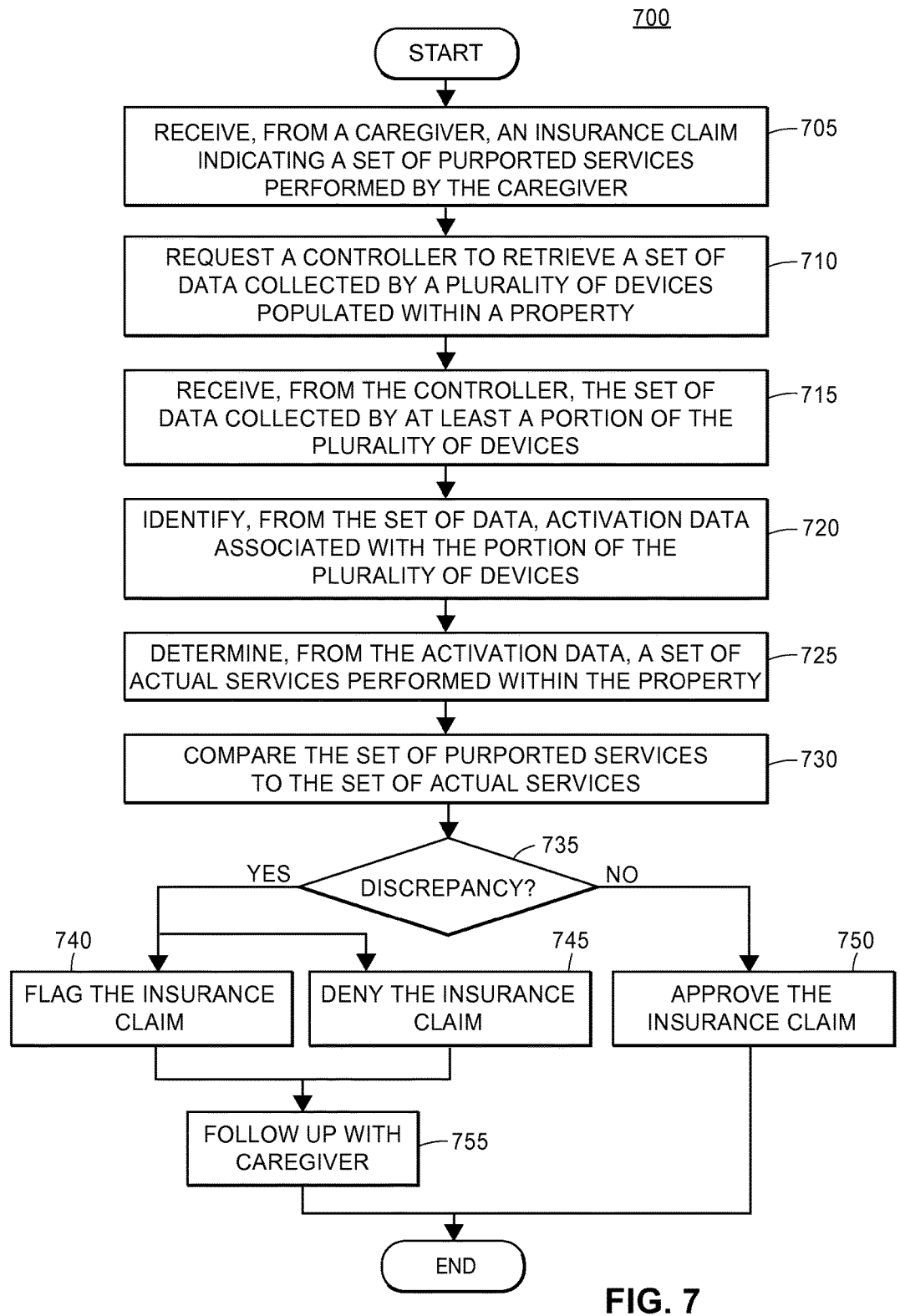
FIG. 7 depicts an exemplary flow diagram associated with detecting inaccuracies in filed insurance claims for long-term care insurance policies, in accordance with some embodiments.

Referring to FIG. 7, depicted is a block diagram of an exemplary method 700 of processing an insurance claim associated with a long-term care insurance policy held by a customer residing in a property. According to embodiments, the property may be populated with a plurality of devices and a controller (such as the controller 120 as discussed with respect to FIG. 1) connected to the plurality of devices. The method 700 may be facilitated by an insurance provider (such as the insurance provider 130 as discussed with respect to FIG. 1) in communication with the controller 120 as well as a caregiver.

The method 700 may begin when the insurance provider receives (block 705), from the caregiver, an insurance claim indicating a set of purported services performed by the caregiver. In particular, the insurance claim can detail services included in the long-term care insurance policy and that the caregiver claims that he/she has performed, as well as a claimed value for each of the purported services. The insurance provider can request (block 710) the controller to retrieve a set of data, such as operation data, collected by the plurality of devices. In some implementations, the insurance provider may specify which of the plurality of devices from which to retrieve data. For example, if the insurance claim indicates a bathing, then the insurance provider may request operation data from a bathtub faucet. Upon receipt of the request, the controller may retrieve the appropriate set of data from at least a portion of the plurality of devices.

At block 715, the insurance provider may receive, from the controller, the set of data collected by at least the portion of the plurality of devices. The insurance provider may also identify (block 720), from the set of data, activation data associated with the portion of the plurality of devices. In particular, the activation data may indicate when certain of the devices are turned on and turned off, as well as other operation data including setpoints, energy usage, operation time, and/or other data indicating operation or use of the corresponding device. Based on the activation data, the insurance provider may determine (block 725) a set of actual services performed within the property. In particular, the insurance provider may access a listing of default services as well as corresponding data that may indicate an operation sequence or data consistent with performance of the service. If the received set of data is similar to one of the operation sequences, then the insurance provider may determine that the corresponding service was actually performed.

After determining the set of actual services, the insurance provider may compare (block 730) the set of purported services to the set of actual services. In particular, the insurance provider may identify (block 735) any discrepancies by identifying any services that are included in the set of purported services and not included in the set of actual services, or any services that are included in the set of actual services and not included in the set of purported services. The insurance provider may also identify any discrepancies in claimed values of the services and actual values of the services. If there are any discrepancies ("YES"), the insurance provider may either flag (block 740) the insurance claim or deny (block 745) the insurance claim. The determination may be based on the degree of discrepancy between the set of purported services and the set of actual services. The insurance provider may also follow up (block 755) with the caregiver accordingly, such as by communicating with the caregiver, in an attempt to clarify or reconcile the discrepancies or otherwise to receive additional information. If there are not any discrepancies ("NO"), the insurance provider may approve (block 750) the insurance claim, and provide an appropriate insurance payout to the caregiver.

Figure 8:
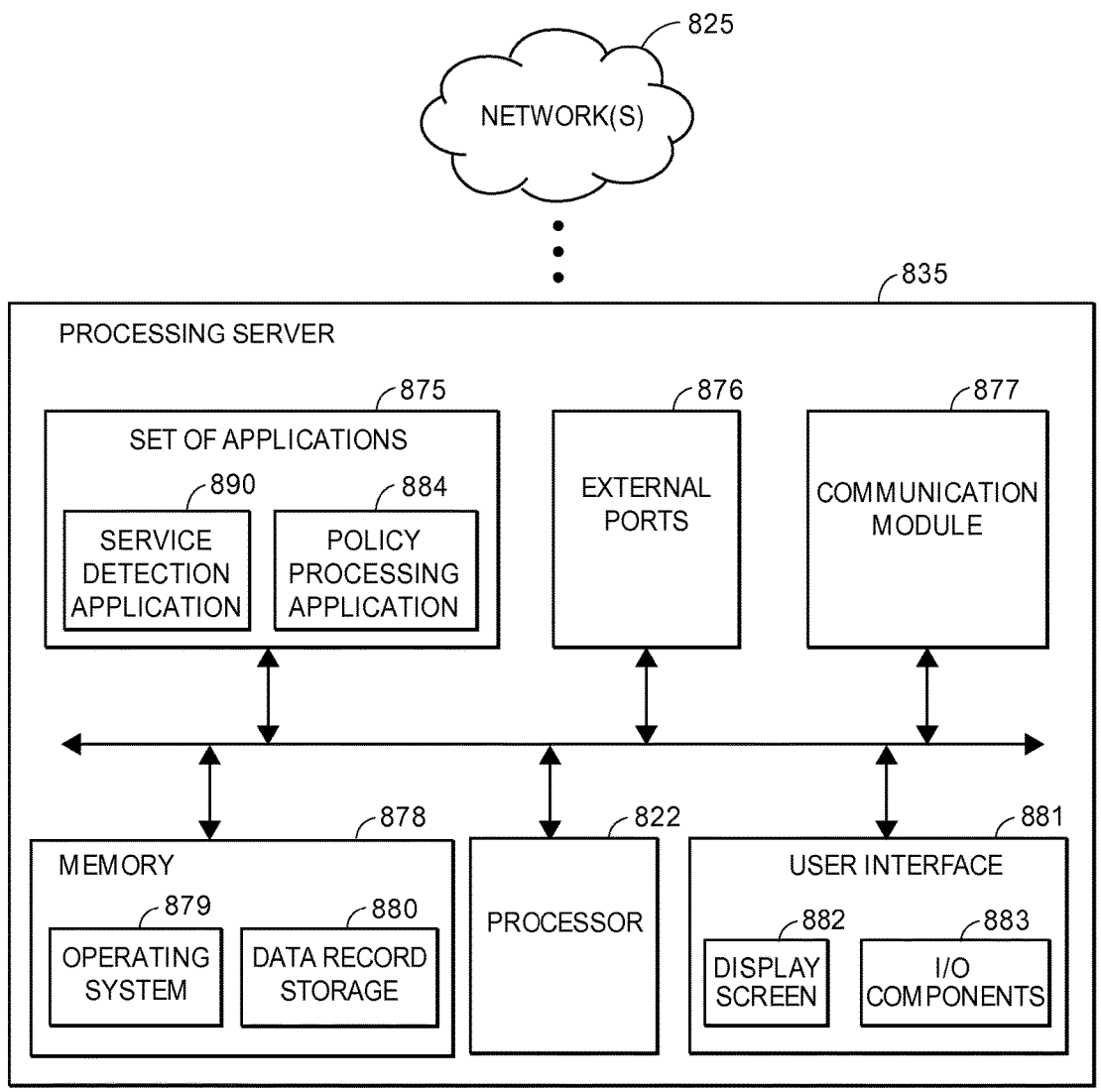
FIG. 8 is a block diagram of an exemplary processing server in accordance with some embodiments.

FIG. 8 illustrates a diagram of an exemplary processing server 835 (such as the processing server 135 discussed with respect to FIG. 1) in which the functionalities as discussed herein may be implemented. It should be appreciated that the processing server 835 may be associated with an insurance provider, as discussed herein.

The processing server 835 may include a processor 822 as well as a memory 878. The memory 878 may store an operating system 879 capable of facilitating the functionalities as discussed herein as well as a set of applications 875 (i.e., machine readable instructions). For example, one of the set of applications 875 may be a policy processing application 884 configured to manage customer insurance policies, and a service detection application 890 configured to identify rendered services based on operation data. It should be appreciated that other applications are envisioned.

The processor 822 may interface with the memory 878 to execute the operating system 879 and the set of applications 875. According to some embodiments, the memory 878 may also include a data record storage 880 that stores various information associated with customer insurance policies. The policy processing application 884 may interface with the data record storage 880 to retrieve relevant information that the policy processing application 884 may use to manage insurance policies, generate notifications, and/or perform other functionalities. The memory 878 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others.

The processing server 835 may further include a communication module 877 configured to communicate data via one or more networks 825. According to some embodiments, the communication module 877 may include one or more transceivers (e.g., WWAN, WLAN, and/or WPAN transceivers) functioning in accordance with IEEE standards, 3GPP standards, or other standards, and configured to receive and transmit data via one or more external ports 876. For example, the communication module 877 may receive, via the network 825, proposed insurance claims from user devices or hardware components associated with properties. The processing server 825 may further include a user interface 881 configured to present information to a user and/or receive inputs from the user. As shown in FIG. 8, the user interface 881 may include a display screen 882 and I/O components 883 (e.g., ports, capacitive or resistive touch sensitive input panels, keys, buttons, lights, LEDs, speakers, microphones). According to some embodiments, the user may access the processing server 835 via the user interface 881 to process insurance policies and/or perform other functions. In some embodiments, the processing server 835 may perform the functionalities as discussed herein as part of a "cloud" network or may otherwise communicate with other hardware or software components within the cloud to send, retrieve, or otherwise analyze data.

Figure 9:
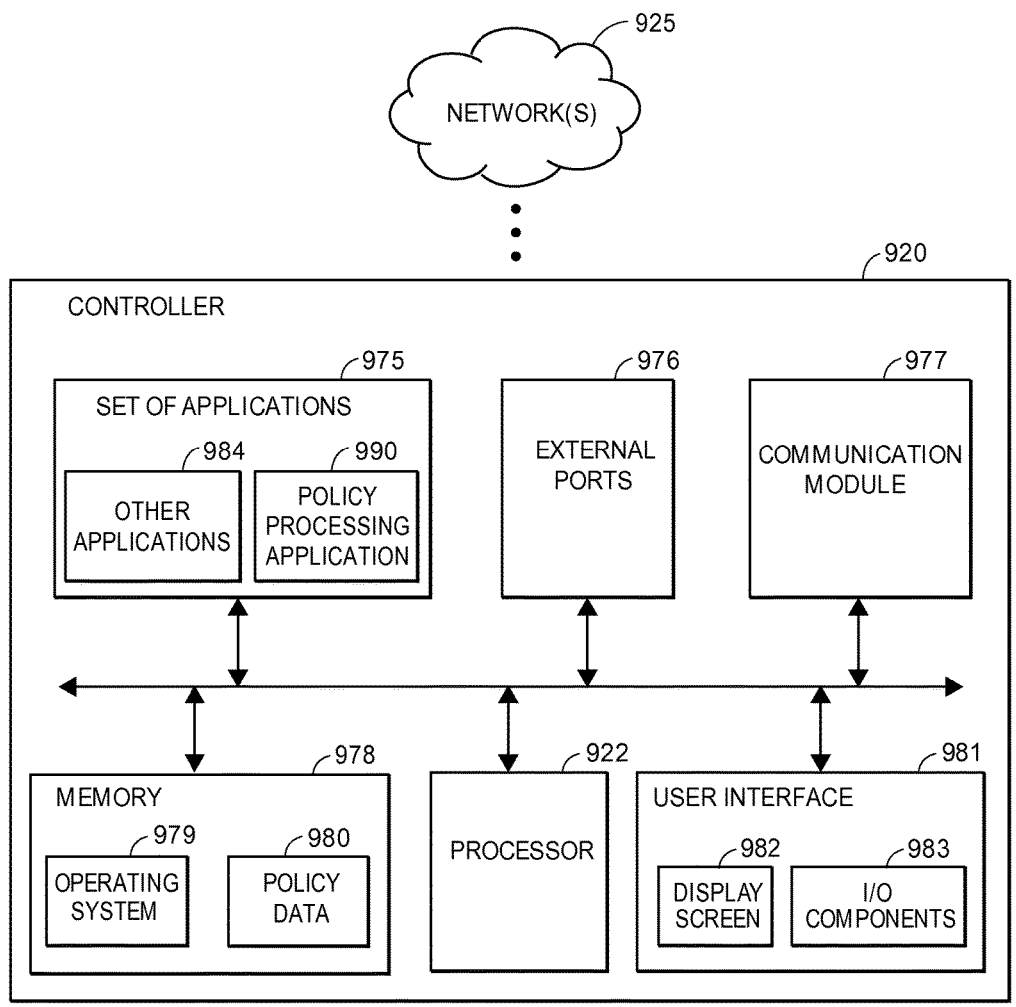
FIG. 9 is a block diagram of an exemplary controller in accordance with some embodiments.

FIG. 9 illustrates a diagram of an exemplary controller 920 (such as the controller 120 discussed with respect to FIG. 1) in which the functionalities as discussed herein may be implemented. It should be appreciated that the controller 920 may be associated with a property, as discussed herein.

The controller 920 may include a processor 922 as well as a memory 978. The memory 978 may store an operating system 979 capable of facilitating the functionalities as discussed herein as well as a set of applications 975 (i.e., machine readable instructions). For instance, one of the set of applications 975 may be a policy processing application 990 configured to access and process customer insurance policies such as long-term care insurance policies. It should be appreciated that other applications 984 are envisioned.

The processor 922 may interface with the memory 978 to execute the operating system 979 and the set of applications 975. According to some embodiments, the memory 978 may also store policy data 980 that stores various data and information associated with long-term care insurance policies. In particular, the policy data 980 may include configuration data associated with devices associated with property. The policy processing application 990 may interface with the policy data 980 to retrieve relevant configuration data and other information that the policy processing application 990 may use to access insurance policies, identify qualified discounts, modify insurance policies, and/or perform other functionalities. The memory 978 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others.

The controller 920 may further include a communication module 977 configured to communicate data via one or more networks 925. According to some embodiments, the communication module 977 may include one or more transceivers (e.g., WWAN, WLAN, and/or WPAN transceivers) functioning in accordance with IEEE standards, 3GPP standards, or other standards, and configured to receive and transmit data via one or more external ports 976. Further, the communication module 977 may include a short-range network component (e.g., an RFID reader) configured for short-range network communications. For instance, the communication module 977 may receive, via the network 925, configuration data from a plurality of devices populated within a property.

The controller 920 may further include a user interface 981 configured to present information to a user and/or receive inputs from the user. As shown in FIG. 9, the user interface 981 may include a display screen 982 and I/O components 983 (e.g., ports, capacitive or resistive touch sensitive input panels, keys, buttons, lights, LEDs, speakers, microphones). According to some embodiments, the user may access the controller 920 via the user interface 981 to process insurance policies and/or perform other functions. The controller 920 may be configured to perform insurance-related functions, such as accessing and modifying long-term care insurance policies. The controller 920 may be also be configured to facilitate modification(s) to a long-term care insurance policy with a remote insurance provider, such as via the network 925. In some embodiments, the controller 920 may perform the functionalities as discussed herein as part of a "cloud" network or may otherwise communicate with other hardware or software components within the cloud to send, retrieve, or otherwise analyze data.

In general, a computer program product in accordance with an embodiment may include a computer usable storage medium (e.g., standard random access memory (RAM), an optical disc, a universal serial bus (USB) drive, or the like) having computer-readable program code embodied therein, wherein the computer-readable program code may be adapted to be executed by the processors 822, 922 (e.g., working in connection with the operating system 879, 979) to facilitate the functions as described herein. In this regard, the program code may be implemented in any desired language, and may be implemented as machine code, assembly code, byte code, interpretable source code or the like (e.g., via C, C++, Java, Actionscript, Objective-C, Javascript, CSS, XML). In some embodiments, the computer program product may be part of a cloud network of resources.

As used herein, the term "smart" may refer to devices, sensors, or appliances located within or proximate to a property, and with the ability to communicate information about the status of the device, sensor, or appliance and/or receive instructions that control the operation of the device, sensor, or appliance, such as via wired or wireless communication or data transmissions. For example, a smart thermostat may be able to remotely communicate the current temperature of the home and receive instructions to adjust the temperature to a new level. As another example, a smart water tank may be able to remotely communicate the water level contained therein and receive instructions to restrict the flow of water leaving the tank. In contrast, "dumb" devices, sensors, or appliances located within or proximate to a property may require manual control. Referring again to the thermostat example, to adjust the temperature on a "dumb" thermostat, a person may have to manually interact with the thermostat. As such, a person may be unable to use a communication network to remotely adjust a "dumb" device, sensor, or appliance.

A "smart device" as used herein may refer to any of a smart device, sensor, appliance, and/or other smart equipment that may be located (or disposed) within or proximate to a property. In some embodiments in which an appliance and a sensor external to the particular appliance are associated with each other, "smart device" may refer to both the external sensors and the appliance collectively. Some examples of devices that may be "smart devices" are, without limitation, valves, piping, clothes washers/dryers, dish washers, refrigerators, sprinkler systems, toilets, showers, sinks, soil monitors, doors, locks, windows, shutters, ovens, grills, fire places, furnaces, lighting, sump pumps, security cameras, and alarm systems. Similarly, an individual associated with the property shall be referred to as the "homeowner," "property owner," or "policyholder," but it is also envisioned that the individual may be a family member of the homeowner, a person renting/subletting the property, a person living or working on the property, a neighbor of the property, or any other individual that may have an interest in preventing or mitigating damage to the property.

Further, any reference to "home" or "property" is meant to be exemplary and not limiting. The systems and methods described herein may be applied to any property, such as homes, offices, farms, lots, parks, apartments, condos, and/or other types of properties or buildings. Accordingly, "homeowner" may be used interchangeably with "property owner."

Although the following text sets forth a detailed description of numerous different embodiments, it should be understood that the legal scope of the invention may be defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that may be permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that may be temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it may be communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment, or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment may be included in at least one embodiment. The appearances of the phrase "in one embodiment" in various places in the specification are not necessarily all referring to the same embodiment.

The terms "insurer," "insuring party," and "insurance provider" are used interchangeably herein to generally refer to a party or entity (e.g., a business or other organizational entity) that provides insurance products, e.g., by offering and issuing insurance policies. Typically, but not necessarily, an insurance provider may be an insurance company.

Although the embodiments discussed herein relate to long-term care insurance policies, it should be appreciated that an insurance provider may offer or provide one or more different types of insurance policies. Other types of insurance policies may include, for example, property insurance, condominium owner insurance, renter's insurance, life insurance (e.g., whole-life, universal, variable, term), health insurance, disability insurance, annuities, business insurance (e.g., property, liability, commercial auto, workers compensation, professional and specialty liability, inland marine and mobile property, surety and fidelity bonds), automobile insurance, boat insurance, insurance for catastrophic events such as flood, fire, volcano damage and the like, motorcycle insurance, farm and ranch insurance, personal liability insurance, personal umbrella insurance, community organization insurance (e.g., for associations, religious organizations, cooperatives), and other types of insurance products. In embodiments as described herein, the insurance providers process claims related to insurance policies that cover one or more properties (e.g., homes, automobiles, personal property), although processing other insurance policies may also be envisioned.

The terms "insured," "insured party," "policyholder," "customer," "claimant," and "potential claimant" are used interchangeably herein to refer to a person, party, or entity (e.g., a business or other organizational entity) that is covered by the insurance policy, e.g., whose insured article or entity (e.g., property, life, health, auto, home, business) is covered by the policy. A "guarantor," as used herein, generally refers to a person, party or entity that is responsible for payment of the insurance premiums. The guarantor may or may not be the same party as the insured, such as in situations when a guarantor has power of attorney for the insured. An "annuitant," as referred to herein, generally refers to a person, party or entity that is entitled to receive benefits from an annuity insurance product offered by the insuring party. The annuitant may or may not be the same party as the guarantor.

As used herein, the terms "comprises," "comprising," "may include," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also may include the plural unless it is obvious that it is meant otherwise.

This detailed description is to be construed as examples and does not describe every possible embodiment, as describing every possible embodiment would be impractical, if not impossible. One could implement numerous alternate embodiments, using either current technology or technology developed after the filing date of this application.

What is claimed is:

1. A computer-implemented method of managing a long-term care insurance policy associated with a property, the method comprising:
sending, via one or more processors, to a computing device communicatively connected to a plurality of components installed within the property, a request for the computing device to periodically provide configuration data associated with each of the plurality of components installed within the property;
periodically receiving, from the computing device communicatively connected to the plurality of components installed within the property, via a communication network, configuration data associated with each of the plurality of components installed within the property;
upon periodically receiving the configuration data, periodically examining, via the one or more processors, the configuration data to identify a modification to a configuration of a particular component of the plurality of components installed within the property, the modification to the configuration reflecting a current configuration of at least one modifiable operational condition of the particular component while the particular component is operational within the property;
examining, via the one or more processors, the long-term care insurance policy to identify a listing of configurations associated with care-designed features installed within the property;
determining, by one or more processors, that the modification to the configuration of the particular component installed within the property is not included in the listing of configurations associated with care-designed features installed within the property;
responsive to determining that the modification to the configuration of the particular component installed within the property is not included in the listing of configurations associated with care-designed features installed within the property, analyzing, via the one or more processors, information associated with the particular component installed within the property to identify a discount associated with the long-term care insurance policy; and
providing a notification of the discount to the long-term care insurance policy to an electronic device of an individual associated with the long-term care insurance policy, wherein the electronic device (i) displays, in an interface, an indication of the discount, and (ii) enables the individual to select to apply the discount to the long-term care insurance policy.

2. The computer-implemented method of claim 1, wherein analyzing the information associated with the particular component installed within the property comprises:
examining a listing of discounts associated with configurations associated with installed components to improve safety within the property; and
identifying the discount from the listing of discounts corresponding to the modification to the configuration of the particular component.

3. The computer-implemented method of claim 1, further comprising:
updating the listing of configurations associated with care-designed features installed within the property to reflect the modification to the configuration of the particular component.

4. The computer-implemented method of claim 1, further comprising:
receiving, from a controller device associated with the property, the listing of configurations associated with care-designed features installed within the property; and
processing the long-term care insurance policy based at least on the listing of configurations associated with care-designed features installed within the property.

5. The computer-implemented method of claim 1, wherein receiving the configuration data further comprises:
receiving the configuration data indicating a new component installed within the property.

6. The computer-implemented method of claim 1, further comprising:
receiving, from the electronic device of the individual, an acceptance of the discount.

7. The computer-implemented method of claim 6, further comprising:
applying the discount to the long-term care insurance policy.

8. A system for managing a long-term care insurance policy associated with a property, comprising:
a communication module adapted to communicate data;
a memory adapted to store non-transitory computer executable instructions; and
a processor adapted to interface with the communication module, wherein the processor is configured to execute the non-transitory computer executable instructions to cause the processor to:
send, via the communication module, to a computing device communicatively connected to a plurality of components installed within the property, a request for the computing device to periodically provide configuration data associated with each of the plurality of components installed within the property
periodically receive, via the communication module, from the computing device connected to the plurality of components installed within the property, configuration data associated with each of the plurality of components installed within the property,
upon periodically receiving the configuration data, periodically examine the configuration data to identify a modification to a configuration of a particular component the plurality of components installed within the property, the modification to the configuration reflecting a current configuration of at least one modifiable operational condition of the particular component while the particular component is operational within the property,
examine the long-term care insurance policy to identify a listing of configurations associated with care-designed features installed within the property,
determine that the modification to the configuration of the particular component installed within the property is not included in the listing of configurations associated with the care-designed features installed within the property,
responsive to determining that the modification to the configuration of the particular component installed within the property is not included in the listing of configurations associated with the care-designed features installed within the property, analyze information associated with the particular component installed within the property to identify a discount associated with the long-term care insurance policy, and
provide, via the communication module, a notification of the discount to the long-term care insurance policy to an electronic device of an individual associated with the long-term care insurance policy, wherein the electronic device (i) displays, in an interface, an indication of the discount, and (ii) enables the individual to select to apply the discount to the long-term care insurance policy.

9. The system of claim 8, wherein to analyze the information associated with the particular component installed within the property, the processor is configured to:
   examine a listing of discounts associated with configurations associated with installed components to improve safety within the property, and
   identify the discount from the listing of discounts corresponding to the modification to the configuration of the particular component.

10. The system of claim 8, wherein the processor is configured to execute the non-transitory computer executable instructions to further cause the processor to:
    update the listing of configurations associated with care-designed features installed within the property to reflect the modification to the configuration of the particular component.

11. The system of claim 8, wherein the processor is configured to execute the non-transitory computer executable instructions to further cause the processor to:
    receive, from a controller device associated with the property via the communication module, the listing of configurations associated with care-designed features installed within the property, and
    process the long-term care insurance policy based at least on the listing of configurations associated with care-designed features installed within the property.

12. The system of claim 8, wherein to receive the configuration data, the processor is further configured to:
    receive, via the communication module, the configuration data indicating a new component installed within the property.

13. A controller device connected to a plurality of components within a property and configured to manage a long-term care insurance policy associated with the property, comprising:
    a communication module adapted to communicate data;
    a memory adapted to store non-transitory computer executable instructions; and
    a processor adapted to interface with the communication module, wherein the processor is configured to execute the non-transitory computer executable instructions to cause the processor to:
        periodically collect, via the communication module, from the plurality of components installed within the property, configuration data (i) associated with each of the plurality of components installed within the property,
        upon periodically collecting the configuration data, periodically examine the configuration data to identify a modification to a configuration of a particular component the plurality of components installed within the property, the modification to the configuration reflecting a current configuration of at least one modifiable operational condition of the particular component while the particular component is operational within the property,
        access the long-term care insurance policy to identify a listing of configurations associated with care-designed features installed within the property,
        determine that the modification to the configuration of the particular component installed within the property is not included in the listing of configurations associated with the care-designed features installed within the property,
        responsive to determining that the modification to the configuration of the particular component installed within the property is not included in the listing of configurations associated with the care-designed features installed within the property, analyze information associated with the particular component installed within the property to identify a discount associated with the long-term care insurance policy, and
        cause a notification of the discount to the long-term care insurance policy to be provided to an electronic device of an individual associated with the long-term care insurance policy, wherein the electronic device (i) displays, in an interface, an indication of the discount, and (ii) enables the individual to select to apply the discount to the long-term care insurance policy.

14. The controller of claim 13, wherein to collect the configuration data associated with the plurality of components within the property, the processor is further configured to:
    detect an installation of a new component within the property, and
    retrieve the configuration data from the new component.

* * * * *